(12) United States Patent
Schader

(10) Patent No.: US 7,753,263 B2
(45) Date of Patent: Jul. 13, 2010

(54) AUTOMATIC CASE DETERMINATION AND ASSIGNMENT

(75) Inventor: Jens Schader, Mannheim (DE)

(73) Assignee: SAP AG, Walldorf (DE)

( * ) Notice: Subject to any disclaimer, the term of this patent is extended or adjusted under 35 U.S.C. 154(b) by 1107 days.

(21) Appl. No.: 11/416,637

(22) Filed: May 2, 2006

(65) Prior Publication Data

US 2007/0260501 A1 Nov. 8, 2007

(51) Int. Cl.
*G06K 5/00* (2006.01)
(52) U.S. Cl. .............................. 235/380; 705/3; 705/9; 705/14; 705/37; 705/59
(58) Field of Classification Search ................ 235/380; 705/3, 37, 59, 14
See application file for complete search history.

(56) References Cited

U.S. PATENT DOCUMENTS

| | | | |
|---|---|---|---|
| 6,424,951 B1 * | 7/2002 | Shurling et al. ............... | 705/14 |
| 7,079,044 B1 * | 7/2006 | Stanfield et al. ........ | 340/825.49 |
| 2002/0107809 A1 * | 8/2002 | Biddle et al. .................. | 705/59 |
| 2002/0169637 A1 * | 11/2002 | Akers et al. .................... | 705/3 |
| 2004/0034550 A1 * | 2/2004 | Menschik et al. .............. | 705/3 |
| 2007/0168401 A1 * | 7/2007 | Kapoor et al. ............. | 707/202 |
| 2009/0076946 A1 * | 3/2009 | Kelly et al. ................... | 705/37 |

* cited by examiner

*Primary Examiner*—Allyson N Trail
(74) *Attorney, Agent, or Firm*—Kenyon & Kenyon LLP

(57) ABSTRACT

In a method and system for automatic case determination and assignment for a business transaction, upon creation of a transaction, a computer system verifies transaction data to determine whether the transaction is assigned to a case. If the transaction is not assigned to a case, the system searches a database for an existing case that is related to the unassigned transaction. If an existing case is discovered, the transaction is automatically assigned to the existing case. If no existing case is found, the system creates a new case, defines new case parameters, and automatically assigns the transaction to the new case.

25 Claims, 8 Drawing Sheets

800 ers and financial services employees then read the applications, contracts, or orders and organize or file them under the appropriate case. In this context, the term "case" may be a general term referring to a centralized holding area, such as in a rudimentary sense a file folder, organized to contain all relevant information and applications for a specific person, company, or transaction. For the social services sector, cases also may be organized by specific benefit applications or by applicants. Following a review process, social services benefits may be dispensed to the applicant claiming them, and financial services, such as credit cards or bank accounts, may be approved.

AUTOMATIC CASE DETERMINATION AND ASSIGNMENT

BACKGROUND

Industries with paperwork-intensive activities typically suffer from a high cost associated with maintaining and organizing large amounts of paperwork. Such industries may include but are not limited to social services and financial services. In social services, a person claiming benefits, from a government social services program or a private sector employer, ordinarily needs to complete an application or other documentation prior to receiving the needed benefit or care. Also, an employer seeking to recover reimbursements for financial benefits paid out to its employees may have to fill out an application or other documentation. Similarly, in the financial services industry, a person applying for a credit card or new bank account, among other things, may have to fill out an application or other documentation. Also, corporations entering into contracts or providing financial services may generate paperwork related to a contract or a service or sales order. Case workers, human resources employees, and financial services employees then read the applications, contracts, or orders and organize or file them under the appropriate case. In this context, the term "case" may be a general term referring to a centralized holding area, such as in a rudimentary sense a file folder, organized to contain all relevant information and applications for a specific person, company, or transaction. For the social services sector, cases also may be organized by specific benefit applications or by applicants. Following a review process, social services benefits may be dispensed to the applicant claiming them, and financial services, such as credit cards or bank accounts, may be approved.

Databases and electronic applications have improved the efficiency and reduced the amount of paper used by paperwork-intensive industries, such as social services and financial services. Systems such as a mySAP Customer Relationship Management (CRM) system or an Oracle E-Business Suite CRM system now more efficiently process applications, service orders and contracts and organize and maintain the applications, service orders, and contracts in cases. An advantage of such systems is that applicants may now submit application information electronically, eliminating much of the paperwork. Despite the increased efficiency, case workers and financial services employees still have to determine to which case an application pertains and manually assign to a case for organizational purposes. Given that hundreds, if not thousands, of cases may exist in a database or computer system, manual assignment of an application to a case may take up valuable time from a case worker or financial services employee. Also, if cases are organized by application, multiple or redundant cases may exist in a system for a specific applicant. Manual assignment of applications to cases likewise may result in human error causing the accidental creation of redundant cases for a specific person. Multiple or redundant cases have the effect of requiring a case worker or human resources employee to expended unnecessary additional effort and time when assigning a benefits application to a case.

What is needed instead is a method for automatically determining an applicable case to which an application is assigned. A method for automatically assigning the application to the identified applicable case may also increase the productivity and efficiency of case workers and financial services employees.

BRIEF DESCRIPTION OF THE DRAWINGS

FIG. 7 is an image illustrating one embodiment of a graphical interface for the manual assignment of a transaction to a new or existing case.

DETAILED DESCRIPTION

Embodiments of the present invention provide a method and system for automatic determination of a case and assignment of a business transaction to the case. Upon creation of a business transaction, such as an application for benefits, transaction data is verified to determine if the transaction is already assigned to a case. If the transaction does not have an existing assignment, a database is searched for an existing case that is related to the transaction. If an applicable existing case is found, the transaction is automatically assigned to the case. If no existing case is found, then a new case is created and new case parameters are defined. The transaction is then automatically assigned to the newly created case.

Figure 1:
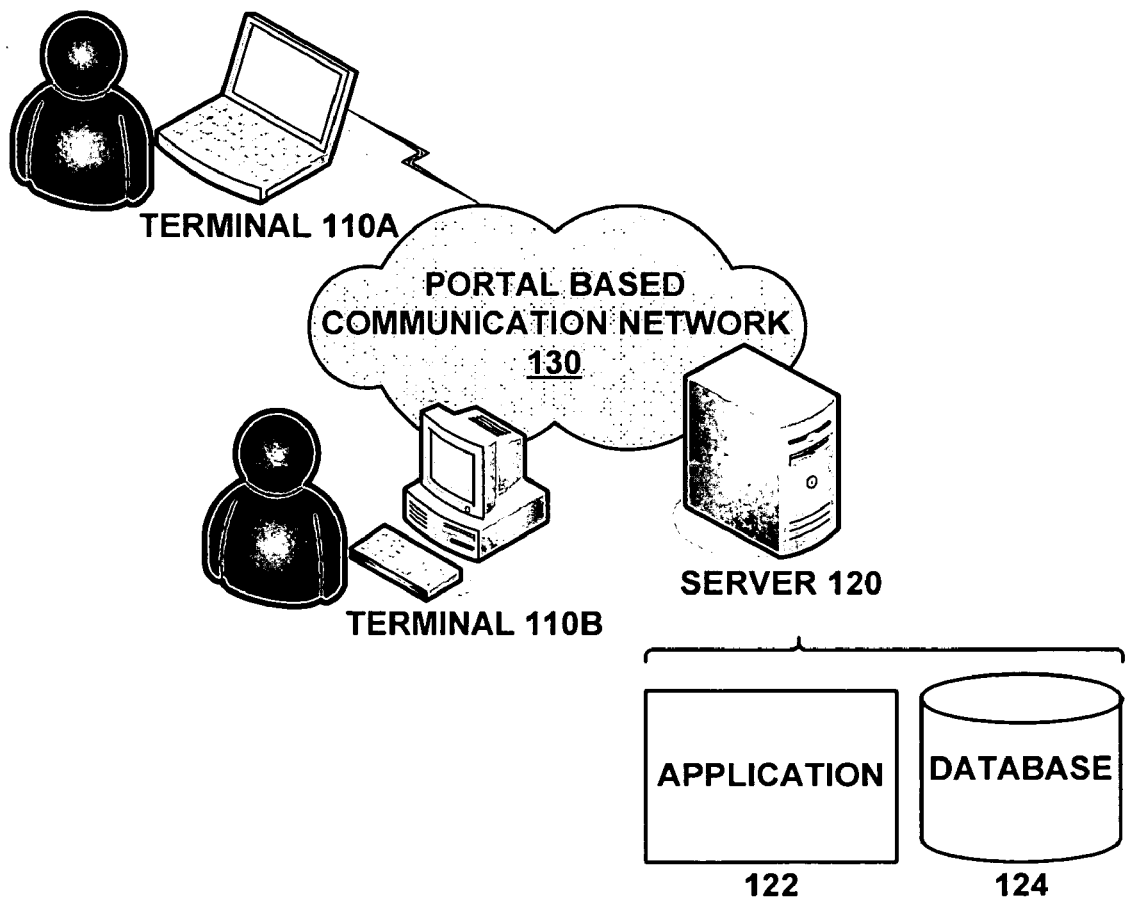
FIG. 1 is a block diagram illustrating a computer network 100 according to an embodiment of the present invention.

FIG. 1 is a block diagram illustrating a computer system 100 according to an embodiment of the present invention. The system 100 may include various terminal(s) 110 and server(s) 120 interconnected by a communication network 130. The server(s) 120 may execute applications 122 and operate on application datasets 124 to manage cases. The terminals 110 may provide communication support with the server(s) to permit operators to interact with the applications and obtain service. As shown in the example of FIG. 1, an employee, such as a case worker or a financial services worker, may interact with a server 120 from a first terminal 110A to manage cases. Also shown in FIG. 1, an applicant may interact with the server 120 from another terminal 110B to apply for benefits. The application 122 may manage interaction with the terminals supporting the employee and the applicant as dictated by its programming. The network 130 may support portal-based communication with the terminals. Various network topologies and system architectures may be used advantageously with the embodiments described hereinbelow; differences among such topologies and architectures are immaterial to the present discussion unless otherwise noted.

Figure 2:
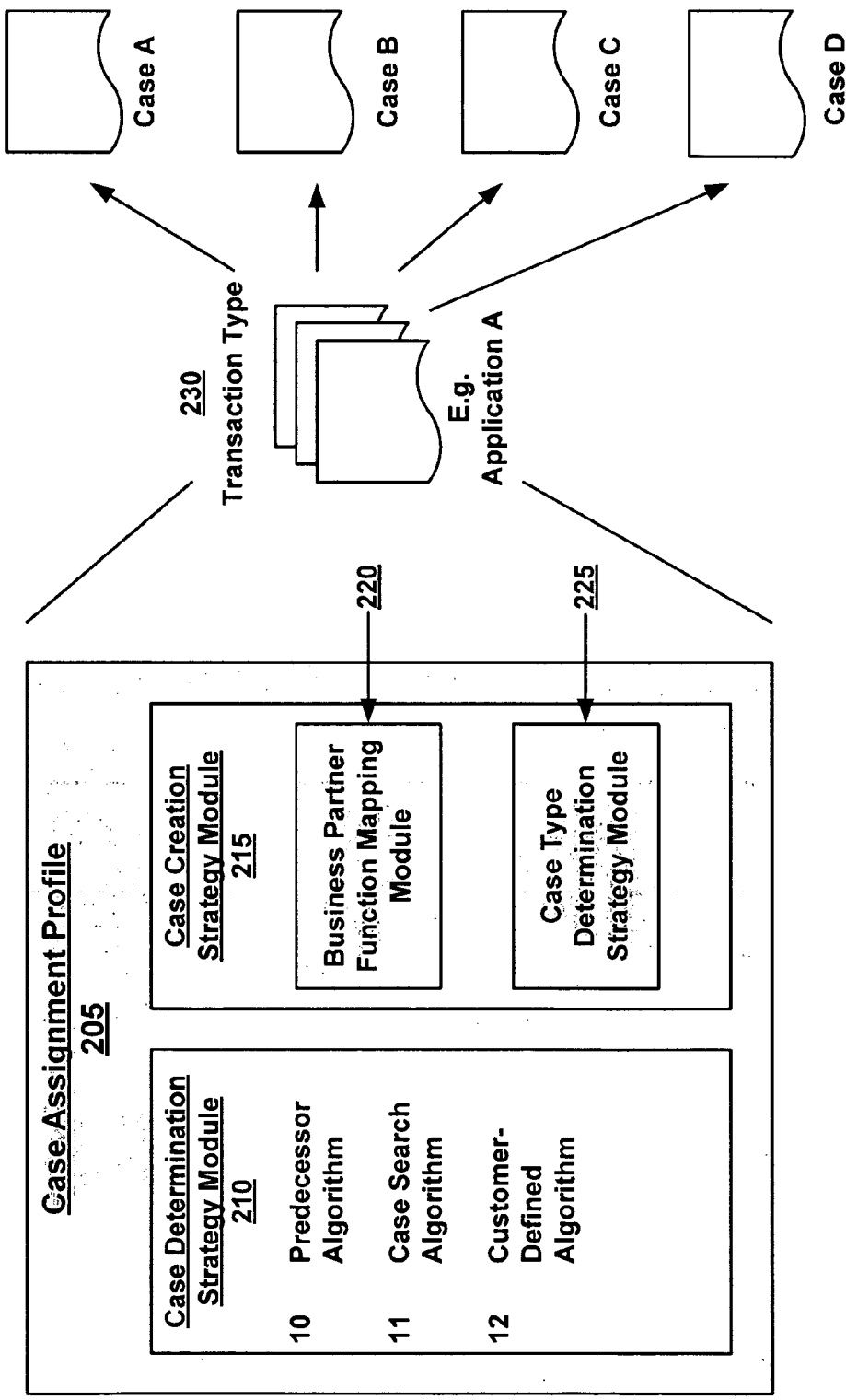
FIG. 2 is a diagram illustrating a modular view of the automatic case determination and assignment process.

FIG. 2 is a diagram illustrating a modular view of the automatic case determination and assignment process. In the network of FIG. 1, a server(s) 120, such as a database, applications, or file server, may store application datasets 124. Application datasets 124 may include case records, business transaction records, such as applications, orders, or contracts, and business transaction types. A case record may be a centralized location storing one or more business transactions pertaining to a particular individual or company. Within the context of a CRM system, a business transaction may provide business structures and functionality that may be used in different aspects of an enterprise, such as in sales, marketing, or services. In the social services context, a business transaction may represent an application submitted by an individual seeking benefits, such as an application for maternity leave, Social Security benefits, or pension benefits. Similarly, in the financial services context, a business transaction may represent an application submitted by applicant seeking to obtain a credit card, open a new bank account, or obtain a line of credit.

Each business transaction also may be based on a business transaction type. Business transaction types may define the characteristics and features of a business transaction. For example, only business transactions involving sales orders may be based on the business transaction type representing sales orders. Business transaction types also may specify the control attributes for a business transaction, such as procedures for determining what business parties may be listed as being involved in the particular business transaction. A business transaction type also may control the processing of a specific business transaction. For example, applications for illness leave, maternity leave, and pension benefits may each be processed differently.

Each transaction type may also be assigned a case assignment profile 205. The case assignment profile may contain protocols for the assignment of a transaction to a new or existing case and protocols for the creation of a new case. These protocols may be embodied in software modules devoted to case determination and case creation. A case determination strategy module may contain predefined or user-defined search algorithms in a specific order that search for an existing case for which to assign a transaction. In the event no existing case is found, a case creation strategy module may determine whether a new case is to be created and may define the case attributes of the new case. Case attributes to be defined by the case creation strategy module may include business partners, business partner functions, case type, and case category.

If an employee submits application data through the portal-based communication network 130 of FIG. 1, the data may be processed and linked or mapped to a particular transaction type to form a business transaction. This newly created transaction containing the application data may then be assigned to a case. Automatic case assignment procedures may be initiated by a case assignment profile 205 assigned to the transaction. The case assignment profile 205 may dictate both how the database searches for existing cases and how a new case may be created. A case determination strategy module 210 in the case assignment profile 205 may store a listing of one or more case search algorithms to use in searching for existing cases. The order of case search algorithms listed in the case determination strategy module 210 may dictate the order in which the algorithms are executed. If a case search algorithm discovers an existing case, the transaction may then be automatically assigned to the discovered case. Any unexecuted case search algorithms in the case search determination module 210 may be disregarded upon the discovery of an existing case.

If no existing case is found, the case assignment profile 205 may employ a case creation strategy module 215 to create a new case and define the parameters and characteristics of the new case. The case creation strategy module 215 may call upon other modules, such as a business partner function mapping module 220 and a case type determination strategy module 225, to define various new case parameters. The business partner function mapping module 220 may define or identify one or more business partners or business partner functions to be assigned to the new case. In one embodiment, the case creation strategy module may then assign the business partners or business partner functions identified or defined by the business partner function mapping module. The business partner function mapping module 220 may also define which business partners or business partner functions may be used by search algorithms to find existing cases. Business partners may be individuals with an interest in the transaction or case, such as an applicant, a beneficiary, or a contact person. A business partner function may identify the role of each business partner within the transaction assigned to the new case. For instance, partner A may be assigned as a business partner to the new case and may have a business partner function of "Applicant" to indicate that the individual A is the applicant seeking benefits. If multiple transactions are assigned to a case, it might be possible for a business partner listed in the multiple transactions to retain different business partner functions.

The case type determination strategy module 225 may define a case type and a case category for a new case. In one embodiment, each new or existing case may be required to have a defined case type. Case types serve as a first level of categorization for cases in a system and may contain various settings, such as an attribute profile, a function profile, a status profile, a text profile, and a terminology profile, that store information relating to the case. Case categories may serve as reference categories for a particular case and may constitute a second level of categorization. Reasons for assigning one or more case categories to a case include process control and hierarchical reporting for cases. Examples of case types might be maternity leave or sick leave, whereas a case category might be the hospital or city where the applicant is giving birth to a child or where the applicant is seeking treatment for an illness. Given case types and case categories, a search algorithm may search for existing cases using these parameters and may retrieve existing cases with matching case types and/or case categories.

Figure 3:
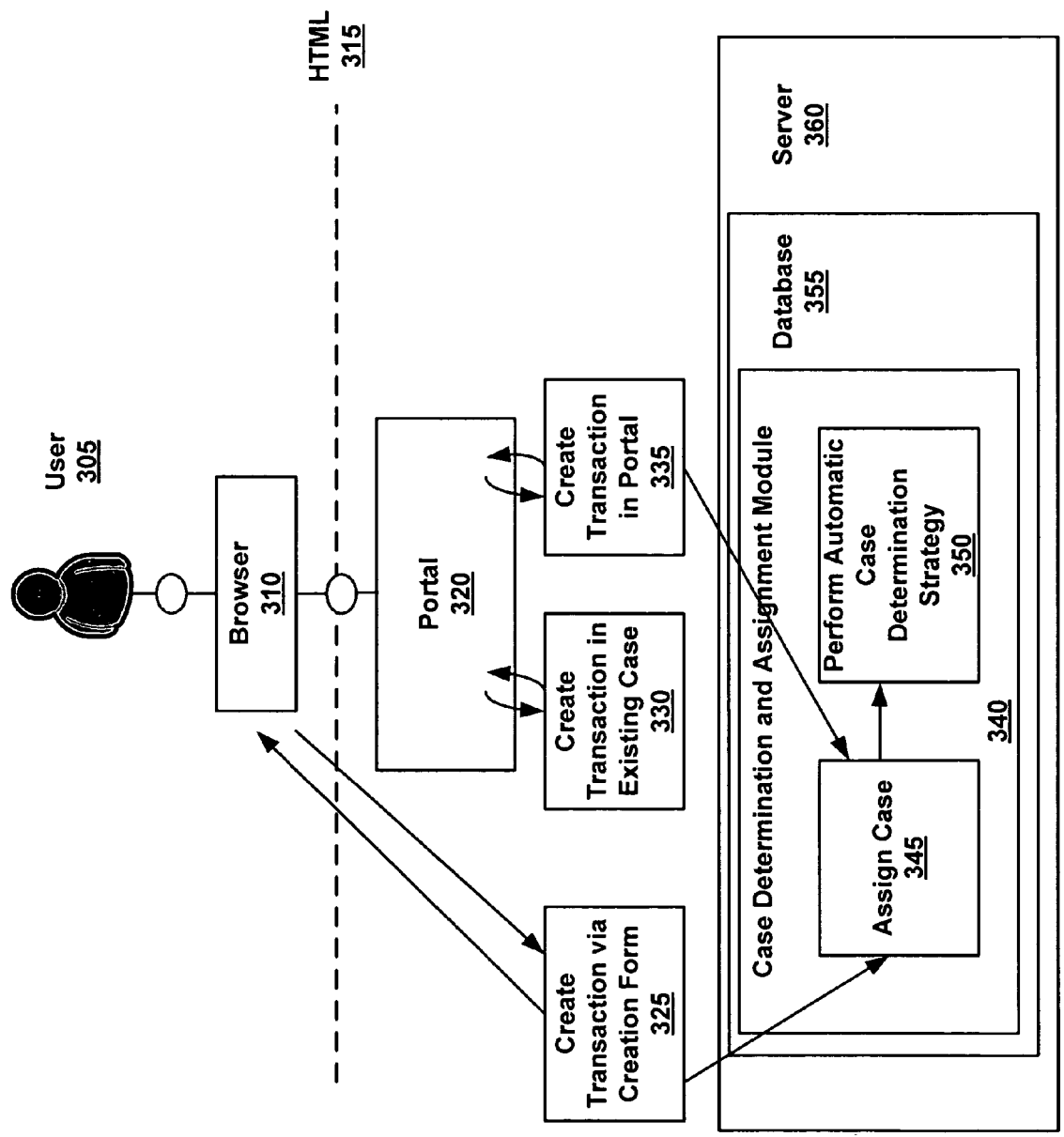
FIG. 3 is a diagram illustrating an embodiment for the processing and assignment of a transaction.

FIG. 3 is a diagram illustrating an embodiment for the processing and assignment of transactions. As illustrated, a user 305 may use a browser application 310 on a computer system, such as Microsoft Internet Explorer or Mozilla Firefox, to access a portal 310. A portal 310 may be an Internet website offering a broad array of resources and services, in this case, related to benefits for both the public and private sector. The portal 320 may also communicate with a server 360 such that any information submitted through the portal 320 is operated on by applications 122, as shown in FIG. 1, resident in the server 360. The database 355 also may store data submitted through the portal 320 and relating to applications and cases for multiple individual applicants or companies. The server 360 may also execute a case determination and assignment application or module 340, embodied in software, to perform the automatic case determination strategy 350, such as searching for existing cases or creating new cases, and to assign newly created transactions to cases.

A user 305, such as a case worker, employee, or applicant, may create a business transaction, such as an application for benefits or an application for financial services. The business transaction may be based on a business object stored within the database. A business object may be regarded as a representation of a tangible or intangible object, such as a concept, business process, or triggering event that is used in conjunction with a business application. Industries or areas in which a user may create business transactions include but are not limited to financial services and social services, such as public sector benefits or private employer benefits. In the financial services context, examples of business transactions may include but are not limited to sales, service orders, and contracts. In the social services context, examples of transactions may include but are not limited to maternity leave benefits, illness benefits, or vacation.

In one embodiment, the user 305, such as a case worker, employee, or applicant, may create a transaction by using a browser application 310 to complete an Internet-based creation form or a form based on an Extensible Markup Language (XML) file 325. Data entered in the creation form or XML form may be linked as an application form to a transaction type based on a business object. If the transaction type linked to the creation form or XML file contains a case assignment profile, the automatic case assignment process may be initiated. A Case Determination and Assignment Module 340 embodied in software and executed by the server 360 may perform the automatic case assignment process to assign the transaction to a new or existing case 345. As part of the automatic case assignment process, the Case Determination and Assignment Module 340 may execute an automatic case determination strategy 350 to search for existing cases or create a new case.

Alternatively, the user 305 may create a transaction by using the browser application 310 to access the portal 320 to communicate with the server 360. The browser application 310 may communicate with the portal 320 through Hypertext Markup Language (HTML) 315, although other computer languages, such as Java, may be used in place of HTML. Using a graphical interface, the case worker may manually select an existing case from the database 355 using application(s) resident on the server 360 and create a transaction within an existing case 330. The transaction may be automatically assigned and directly linked to the case 330, thus rendering any case searching unnecessary. In one embodiment, no case determination strategy (i.e., case search strategy) needs to be maintained in the case assignment profile 205 for the new transaction because the transaction is already linked and assigned to an existing case.

In another embodiment, the user 305 may create a transaction by using the browser application 310 to access the portal 320 to communicate with the server 360. In the portal 320, the user 305 may manually create a new transaction based on an existing transaction type 335. If the transaction type contains a case assignment profile, the Case Determination and Assignment Module 340 may initiate automatic case assignment procedures to assign the transaction to a new or existing case 345. As part of the automatic case assignment procedures, the Case Determination and Assignment Module 340 may perform an automatic case determination strategy to search for existing cases using case search algorithms 350. If no existing cases are found using case search algorithms, the Case Determination and Assignment Module 340 may create a new case and assign case parameters, such as business partners, a case type, and a case category, to the new case before the assignment of the new transaction to the new case.

Figure 4:
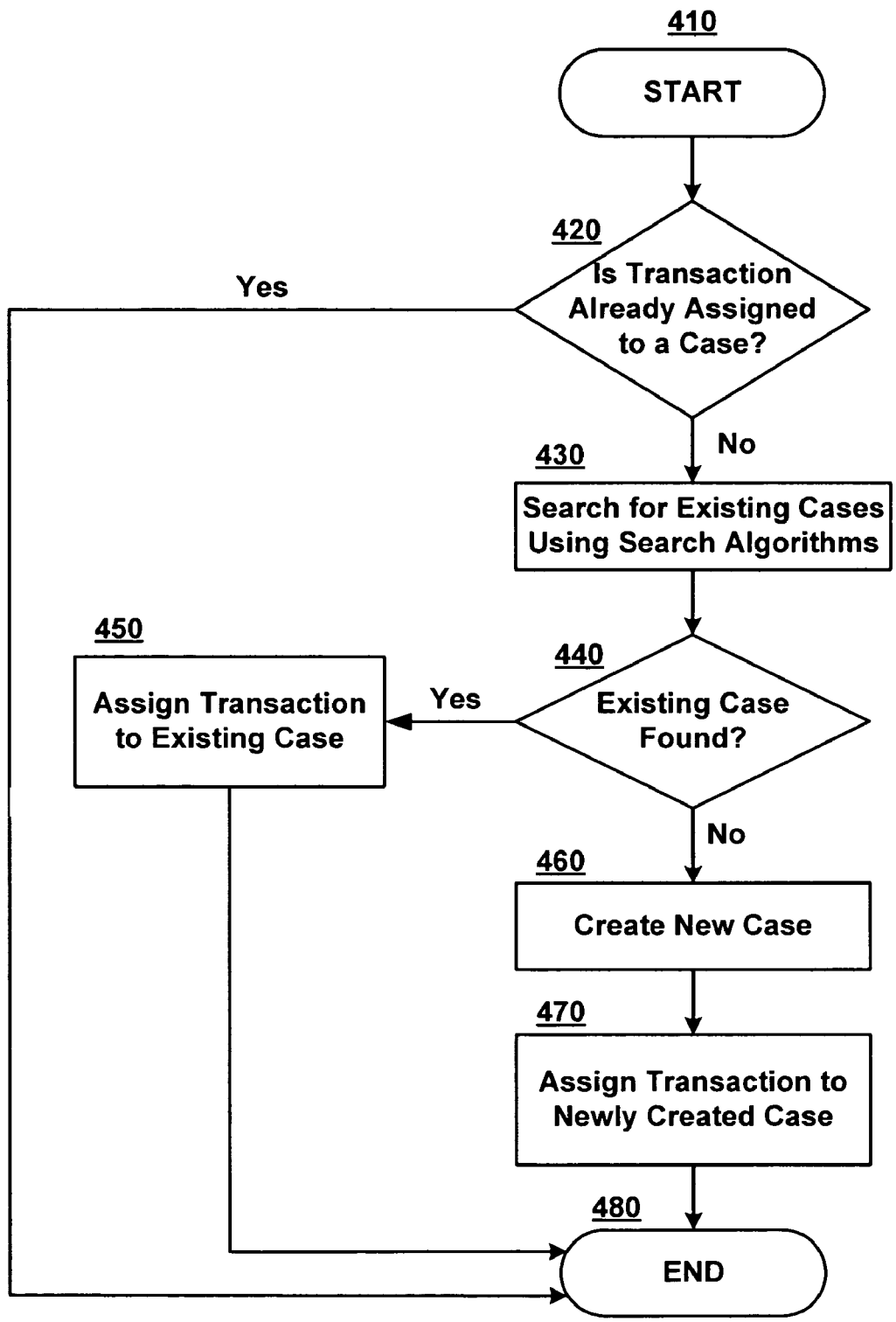
FIG. 4 is a flowchart illustrating one embodiment for automatic case determination and assignment.

FIG. 4 is a flowchart illustrating one embodiment for automatic case determination and assignment. Prior to block 420, a business transaction, such as an application for employee or citizen benefits or an application for a new bank account or credit card, is created. Transactions may be submitted using XML-based forms or other types of electronic or Internet-based forms. In block 420, transaction data may be verified to determine if the transaction is already assigned to a case. As part of the verification, the transaction type, case type, and case category of the transaction may be retrieved. In one embodiment, a function module, embodied in either hardware or software, may be called by a mySAP CRM system, Oracle E-Business Suite CRM system, or a similar system to retrieve the transaction data. Using data representing the transaction type, a system may check for the presence of a case assignment profile for the given transaction to determine whether an automatic case assignment process may be implemented. If a case assignment profile is not present, the automatic case assignment process ends. If a case assignment profile exists for the transaction, then before the automatic case assignment process may begin, the system may retrieve all cases for the given transaction type and corresponding business object. In one embodiment, a different function module may be called by a mySAP CRM system, Oracle E-Business Suite CRM system, or a similar system to retrieve the cases. Based on the results of the case retrieval, the system may determine whether the transaction is already assigned to a case. If the transaction is assigned to a case, then the process ends in block 480.

In block 430, if the transaction is not assigned to a case, the automatic case assignment process may employ case search algorithms to search for an existing case. Each transaction type and corresponding case assignment profile may employ different case search algorithms or the same case search algorithms arranged in a different order. Examples of case search algorithms available may include a "predecessor" algorithm, a "case search" algorithm, and a "customer-defined" algorithm, but are by no means limited to these three algorithms.

In a "predecessor" search algorithm, the search may be performed by analyzing the document flow of the transaction to determine if a predecessor transaction has been assigned to a case. Document flow may refer to a chain of transactions linked together in a business context. For example, if the transaction in question is a transaction entitled "Transaction B" and is a grant of an application for maternity leave, the document flow may reveal a transaction entitled "Transaction A" which is assigned to Case X and is an application for maternity leave. In order to verify that the discovered predecessor transaction is the correct predecessor, the system may verify that the transaction type of the predecessor transaction matches the transaction type of the unassigned transaction. Once a predecessor transaction is identified, the system may determine the case of the predecessor transaction. In a mySAP CRM system, another function module may be called to determine the case of the predecessor transaction; similar functions may exist and be used by other systems, such as an Oracle E-Business Suite CRM system. Once a case is returned, the system may verify the system status of the case to ensure the case is not closed. If the case is open, then the unassigned transaction may be assigned to the case.

In a "case search" algorithm, a search for an existing case may be performed using predefined case parameters, such as case type, case category, business partners, and business partner functions. An example of a case type may be maternity leave benefit or illness benefit. Examples of a case categories for the case type "illness benefit" may be illness in a special situation (case category A) or normal illness (case category B). In one embodiment, in searching for existing cases using the predefined search criteria, only cases with a certain case status may be retrieved. This may ensure that cases with a closed or inactive status are not retrieved. If multiple cases are retrieved, the automatic case assignment process may notify a case worker in order for the case worker to manually select the appropriate existing case. Once an existing case is selected, the transaction may be automatically assigned to the existing case.

In a "customer-defined" algorithm, the system may perform a search for an existing case using customer-defined search criteria. The case worker or customer may use a business rules framework (BRF) to help define search criteria. The BRF is an event-controlled runtime environment for processing business rules and may be a component of a CRM system. Any number of business rules may be assigned to an event, and each business rule may consist of a Boolean expression and an action. If the Boolean expression returns a TRUE result, the system may execute the action. Apart from or in addition to the predefined case parameters (e.g. case type, case category, and business partner), the case worker or customer may provide the system with one or more search criteria in the form of business rules. Cases may be retrieved using these customer-defined parameters. If an existing case is retrieved in block 440, the new transaction may be automatically assigned to the existing case in block 450.

If no existing case is found in block 440, the automatic case assignment process may create a new case, as illustrated in block 460. As part of the automatic case assignment process, the case assignment profile of the transaction may be accessed. The case creation strategy stored in the case assignment profile may be accessed to define how the new case may be created. In block 470, following the creation of the case, the transaction may be automatically assigned to the case. The automatic case determination and assignment process ends in block 480.

Figure 5:
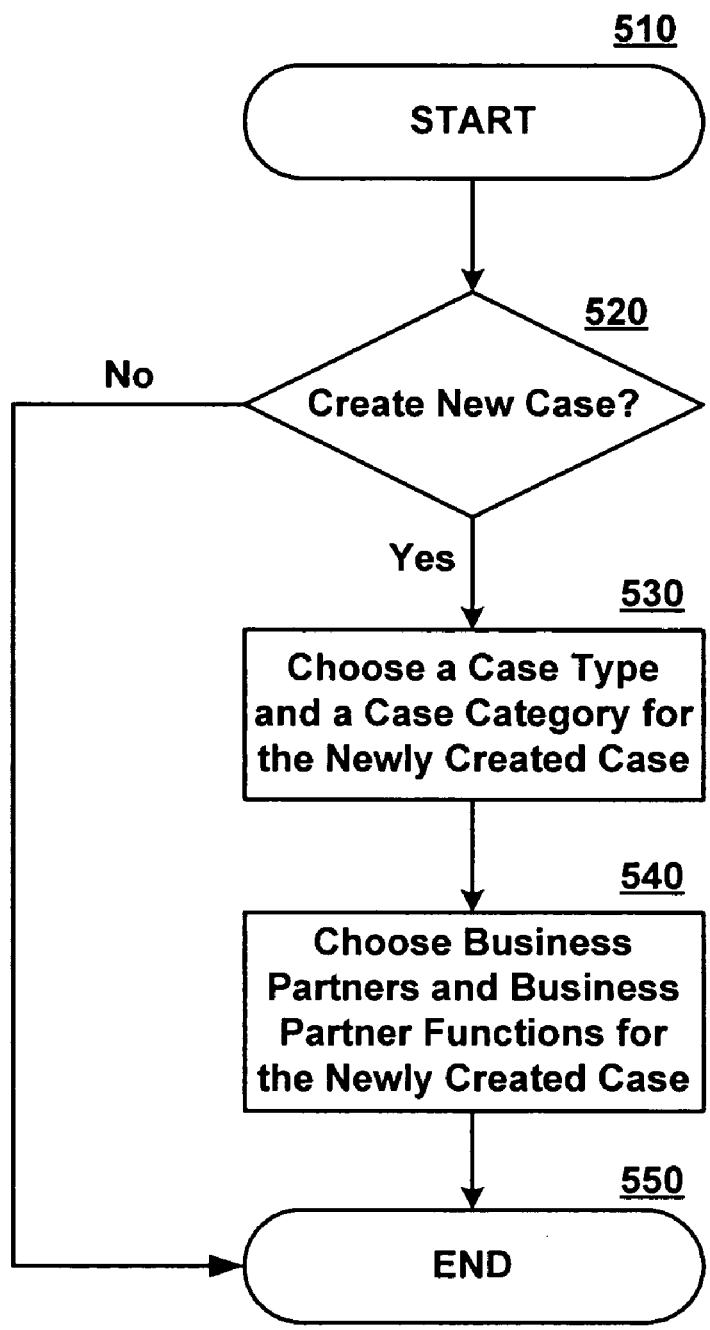
FIG. 5 is a flowchart illustrating one embodiment for creating a new case using an automatic case determination and assignment process.

FIG. 5 is a flowchart illustrating one embodiment for creating a new case using an automatic case determination and assignment process. In block 520, the automatic case determination and assignment process may determine whether a new case is being created. If an existing case has been found, the process ends in block 550. If a new case is to be created, the process proceeds to block 530. In block 530, the case assignment profile of the transaction may be used to define the case type and case category parameters for the new case. In addition, the employee may have the ability to define additional attributes for the new case, including, but not limited to, the title of the case, a description of the case, and the priority of the case. In one embodiment, the case type for the new case may be a mandatory parameter for the new case. Setting a case type for the new case may be mandatory in order to facilitate the ability to discover the new case in future case searches. In block 540, a main business partner and other business partners as well as business partner functions may be assigned to the new case. The main business partner may be the primary contact of a transaction or an individual with the most interest in the transaction, such as the financial services or social services applicant. The main business partner to a case may also have its business partner function designated as "main business partner" to indicate his or her role in the case. Other business partners may be designated as well, such as the name of a contact person for the case or a doctor assigned to treat the applicant. In block 550, the case creation process ends and the transaction may be assigned to the new case.

Figure 6:
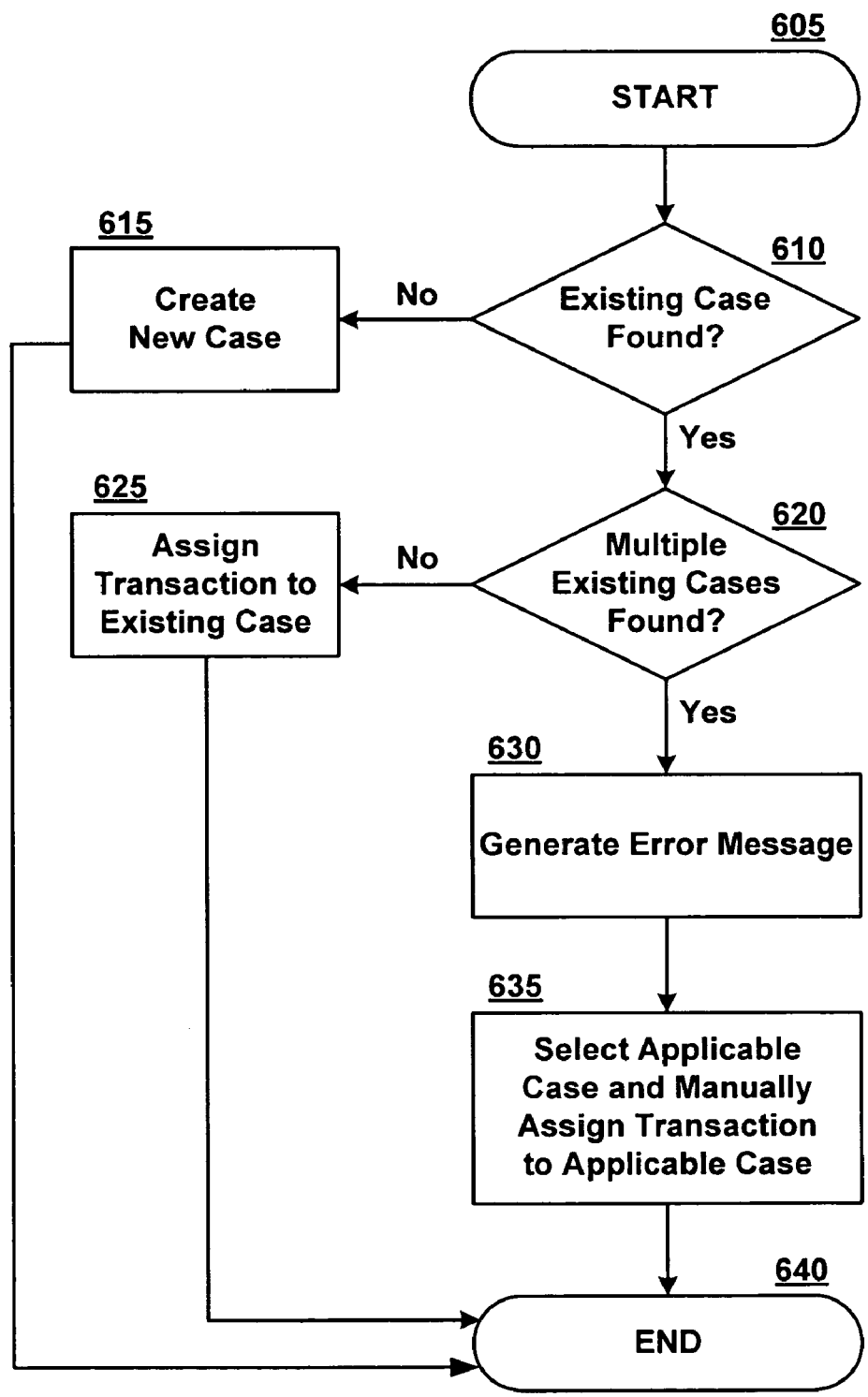
FIG. 6 is a flowchart illustrating an embodiment for the handling of errors generated during the automatic case determination and assignment process.

FIG. 6 is a flowchart illustrating an embodiment for the handling of errors generated during the automatic case determination and assignment process. In block 610, the system may conduct a search and retrieve any existing cases matching the search terms used. If no existing cases are retrieved by the search, then in block 615, a new case may be created. In block 620, the system may determine whether multiple existing cases result from the search. If only one existing case is retrieved from the search, then in block 625, the transaction may be assigned to the retrieved case. If multiple existing cases are retrieved, then in block 630, the system may notify the employee by generating an error message. In block 635, the employee may select the appropriate retrieved case from the list of multiple cases found and manually assign the transaction to the selected case. The process ends in block 640.

Figure 7:
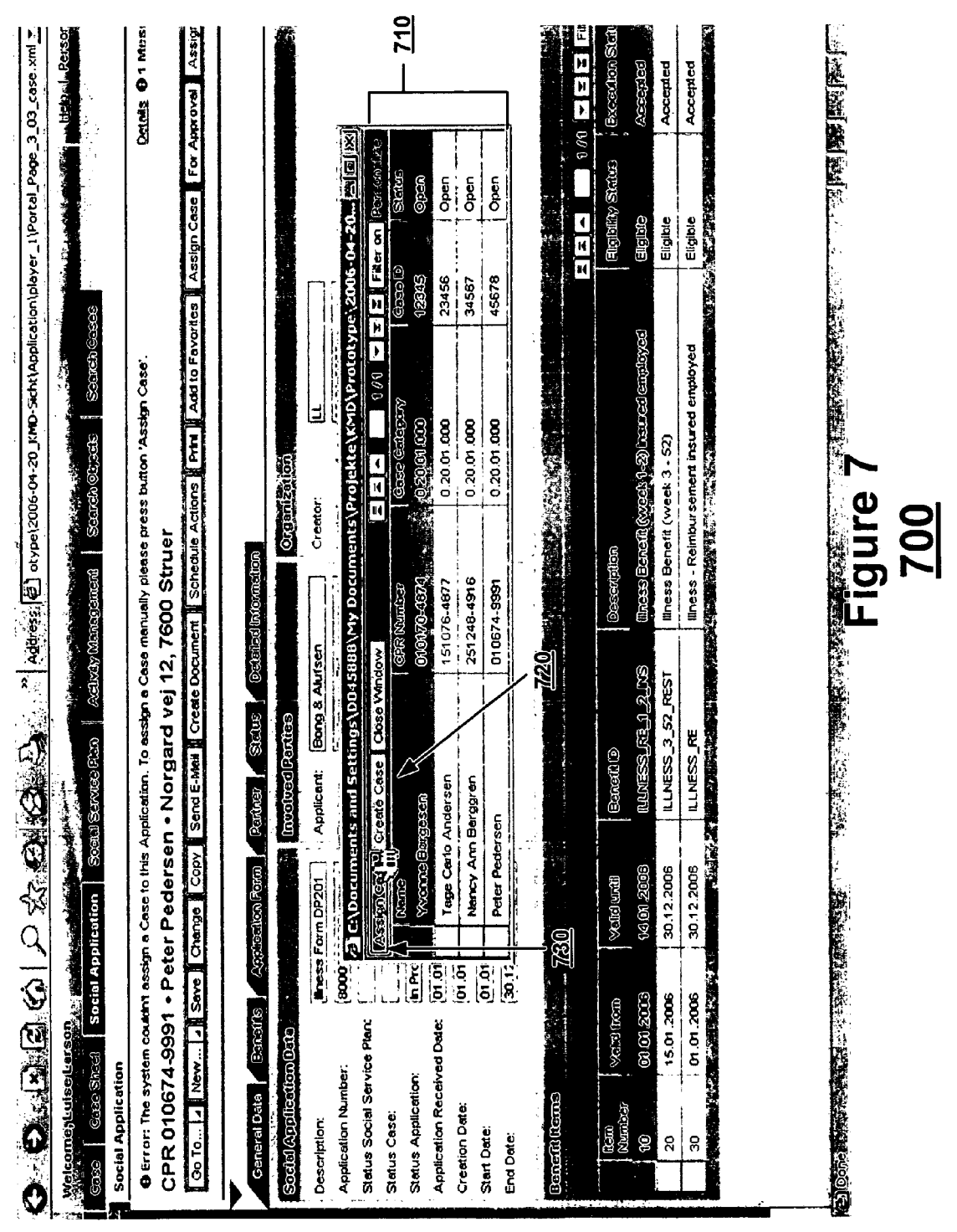

FIG. 7 is an image illustrating one embodiment of a graphical interface for the manual assignment of a transaction to a new or existing case. Using a graphical interface, a Web-based portal may interface the database and server through a network, such as the Internet, or through a terminal with direct access to the database and server. Where multiple existing cases 710 are found following a case search, the employee may manually assign the transaction to an existing case. Existing cases 710 may be displayed in the graphical interface in a table format. The graphical interface may also have button functionality to enable a case worker to click on the "Create Case" button 720 to manually create a new case. In one embodiment, multiple user interfaces may be components of a mySAP CRM system, and the button functionality may be available in a case management user interface rather than a business transaction user interface. In one embodiment, upon clicking on the "Create Case" button 720 to create a new case, the new case may be added to the table of existing cases 710. The employee may highlight the new case or an existing case and click the "Assign Case" button 730 to manually assign the transaction to the highlighted case.

Figure 8:
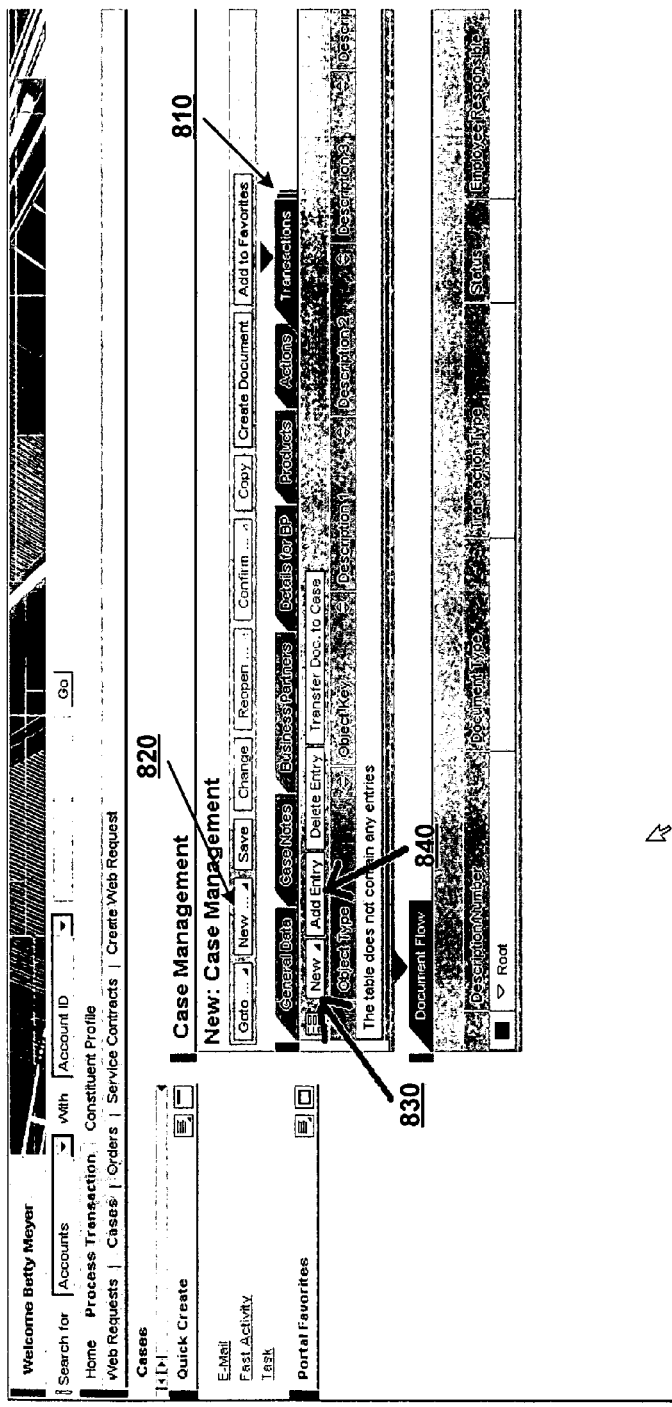
FIG. 8 is an image illustrating one embodiment of a graphical interface for case management.

FIG. 8 is an image illustrating one embodiment of a graphical interface for case management. Through this embodiment of a graphical interface, an employee may manage cases stored in the database. In the case management window, the employee may select a case and view and manage all transactions assigned to the selected case. The employee may also create a new case. By clicking on the "Transactions" tab 810, the employee may assign a new or existing transaction to the selected case. The employee may also view all transactions assigned to the selected case within the "Transactions" tab 810. To create a new case, the employee may click on the "New" button 820 next to the "Goto" button. To create a new business transaction, the employee may click on the "New" button 830. To manually assign an existing transaction found in the "Transactions" tab 810 or the newly created business transaction to an existing case, the employee may click on the "Add Entry" button 830.

While the invention has been described with reference to the above embodiments, it is to be understood that these embodiments are purely exemplary in nature. Thus, the invention is not restricted to the particular forms shown in the foregoing embodiments. Various modifications and alterations can be made thereto without departing from the spirit and scope of the invention.

What is claimed is:

1. A computer-implemented method of automatic case determination and assignment, the method comprising:
   at a server in communication with a user terminal via a network:
      receiving transaction data submitted from the user terminal, the transaction data representing a business transaction having a business transaction type from among a plurality of business transaction types;
      verifying the transaction data to determine if the transaction is assigned to a case;
      if no assignment exists, executing a case determination strategy application maintained in a case assignment profile associated with the business transaction type, the case determination strategy application storing case search algorithms for the business transaction type for searching existing cases maintained in a database;

iteratively searching the database for an existing case that is related to the transaction using each of the stored case search algorithms associated with the business transaction type;

if an existing case is found during the searching, automatically assigning the transaction to the existing case; and if no existing case is found, creating a new case and defining new case parameters and automatically assigning the transaction to the new case.

2. The method of claim 1, wherein the searching occurs by a transaction predecessor algorithm.

3. The method of claim 1, wherein the searching occurs by a case search algorithm based on predefined case parameters.

4. The method of claim 1, wherein the searching occurs by a customer-defined search algorithm.

5. The method of claim 1, wherein the new case parameters include a business partner and a business partner function.

6. The method of claim 1, wherein the new case parameters include a case type and a case category.

7. The method of claim 1, further comprising:

responsive to a successful existing case search, generating an error message if multiple existing cases are found; and manually assigning the transaction to an appropriate existing case selected from the multiple existing cases.

8. The method of claim 1, further comprising:

responsive to a successful existing case search or the new case creation, verifying the assignment of a first business partner to the existing case or the new case; and if no business partner assignment exists, assigning a second business partner listed in the transaction data to the existing case or the new case.

9. A computer-readable storage medium containing a set of instructions, the set of instructions capable of causing a computer to implement a method comprising:

receiving transaction data submitted from the user terminal, the transaction data representing a business transaction having a business transaction type from among a plurality of business transaction types;

verifying the transaction data to determine if the transaction is assigned to a case;

if no assignment exists, executing a case determination strategy application maintained in a case assignment profile associated with the business transaction type, the case determination strategy application storing case search algorithms for the business transaction type for searching existing cases maintained in a database;

iteratively searching the database for an existing case that is related to the transaction using each of the stored case search algorithms associated with the business transaction type;

if an existing case is found during the searching, automatically assigning the transaction to the existing case; and if no existing case is found, creating a new case and defining new case parameters and automatically assigning the transaction to the new case.

10. The computer-readable storage medium of claim 9, wherein the searching occurs by a transaction predecessor algorithm.

11. The computer-readable storage medium of claim 9, wherein the searching occurs by a case search algorithm based on predefined case parameters.

12. The computer-readable storage medium of claim 9, wherein the searching occurs by a algorithm is a customer-defined search algorithm.

13. The computer-readable storage medium of claim 9, wherein the new case parameters include a business partner and a business partner function.

14. The computer-readable storage medium of claim 9, wherein the new case parameters include a case type and a case category.

15. The computer-readable storage medium of claim 9, further comprising:

responsive to a successful existing case search, generating an error message if multiple existing cases are found; and manually assigning the transaction to an appropriate existing case selected from the multiple existing cases.

16. The computer-readable storage medium of claim 9, further comprising:

responsive to a successful existing case search or the new case creation, verifying the assignment of a first business partner to the existing case or the new case; and if no business partner assignment exists, assigning a second business partner contained in the transaction data to the existing case or the new case.

17. A case determination and assignment system, comprising:

a database storing data representing an unassigned transaction having a business transaction type from among a plurality of business transaction types;

a case search module storing case search algorithms for each business transaction type for searching existing cases maintained in a database and operable to iteratively search the database for an existing case that is related to the unassigned transaction using each of the stored search algorithms associated with the business transaction type;

a case creation module operable to create a new case, if no existing case related to the unassigned transaction is found; and a case assignment module operable to automatically assign the unassigned transaction to the existing case or the new case, if no existing case is found.

18. The case determination and assignment system of claim 17, further comprising:

a case determination strategy module operable to store case search algorithms used by the case search module to search the database.

19. The case determination and assignment system of claim 18, wherein the case search algorithms include a transaction predecessor algorithm.

20. The case determination and assignment system of claim 18, wherein the case search algorithms include a case search algorithm based on predefined case search parameters.

21. The case determination and assignment system of claim 18, wherein the case search algorithms include a customer-defined search algorithm.

22. The case determination and assignment system of claim 17, further comprising:

a case creation strategy module operable to define new case parameters for the new case.

23. The case determination and assignment system of claim 17, further comprising:

a business partner function module operable to:

verify assignment of a first business partner and a first business partner function to the existing case or the new case, if no existing case is found; and if no first business partner or first business partner function assignment exists, assign a second business partner and a second business partner function listed in the unassigned transaction data to the existing case or the new case, if no existing case is found.

24. The case determination and assignment system of claim 22, further comprising:

a case type determination module operable to store a plurality of case types and a plurality of case categories, and assign a first case type and a first case category as the new case parameters for the new case.

25. The case determination and assignment system of claim 17, further comprising:

an error handling module operable to generate an error message if multiple existing cases are found, and prompt a user to manually assign the unassigned transaction to an appropriate existing case selected from the multiple existing cases.

* * * * *